US00PP16143P3

(12) United States Plant Patent
Olesen et al.

(10) Patent No.: US PP16,143 P3
(45) Date of Patent: Dec. 6, 2005

(54) ROSE PLANT NAMED 'POULCS012'

(50) Latin Name: *Rosa hybrida*
Varietal Denomination: Poulcs012

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 38 days.

(21) Appl. No.: 10/812,698

(22) Filed: Mar. 29, 2004

(65) Prior Publication Data

US 2005/0216979 P1 Sep. 29, 2005

(51) Int. Cl.[7] ..... A01H 5/00
(52) U.S. Cl. ..... Plt./104
(58) Field of Search ..... Plt./104

(56) References Cited

U.S. PATENT DOCUMENTS

PP9,716 P * 12/1996 Olesen et al. ..... Plt./118
PP12,522 P2 * 4/2002 Olesen et al. ..... Plt./145
2002/0092046 P1 * 7/2002 Evers ..... Plt./104

OTHER PUBLICATIONS

UPOV ROM GTITM Computer Database, GTI Jouve Retrieval Software 2004/04 Citation for 'Poulcs012'.*

* cited by examiner

*Primary Examiner*—Kent Bell
*Assistant Examiner*—W. C. Haas

(57) ABSTRACT

A new garden rose plant of the floribunda class which has abundant, light yellow flowers and attractive foliage. This new and distinct variety has shown to be uniform and stable in the resulting generations from asexual propagation.

2 Drawing Sheets

Botanical classification: *Rosa hybrida.*
Variety denomination: 'Poulcs012'.

SUMMARY OF THE INVENTION

The present invention constitutes a new and distinct variety of garden rose plant which originated from a controlled crossing between the female seed parent, an unnamed seedling, and the male pollen parent 'Poulsun', U.S. Plant Pat. No. 9,716. The two parents were crossed during the summer of 1992 and the resulting seeds were planted in a controlled environment in Fredensborg, Denmark. The new variety named 'Poulcs012' originated as a single seedling from the stated cross.

The new variety may be distinguished from its unnamed female seed parent, by the difference in flower color. While the seed parent has creamy white flowers, 'Poulcs012' has medium yellow flowers.

The new variety may be distinguished from its male pollen parent, 'Poulsun' by the following combination of characteristics:

1. While the pollen parent 'Poulsun' has flower petals which are Yellow Group 13A on the upper surface, 'Poulcs012' has flower petals which are Yellow Group 4C.
2. While the pollen parent reaches a height of 12 inches (30 cm), 'Poulcs012' grows taller, to a height of 60 cm.

The objective of the hybridization of this rose variety was to create a new and distinct variety for garden use with unique qualities, such as:

1. Uniform and abundant light yellow flowers;
2. Vigorous, but compact growth when propagated both as a budded rose and on its own roots;
3. Disease resistance;
4. Continuous flowering.

This combination of qualities is not present in previously available commercial cultivars of this type, known to the inventors, and distinguish 'Poulcs012' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'Poulcs012' was selected in the spring 1993 by the inventors as a single plant from the progeny of the aforementioned hybridization.

Asexual reproduction of 'Poulcs012' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'Poulcs012' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcs012'. Specifically illustrated in the first drawing:

FIG. 1.1; Open flower, stem showing cluster of open flowers, branching, and the attachment of leaves, buds, and peduncles;

FIG. 1.2; Flower bud closed, flower bud as sepals unfold, and partially open;

FIG. 1.3; Flower petals, detached.

Specifically illustrated in the second drawing:

FIG. 2.1; Sepals, receptacle, and peduncle;

FIG. 2.2; Juvenile leaf;

FIG. 2.3; Mature leaves;

FIG. 2.4; Bare stems exhibiting thorns.

DETAILED DESCRIPTION OF THE VARIETY

The following is a description of 'Poulcs012', as observed in its growth in a field nursery in Jackson County, Oreg. Observed plants are 3 years of age. Plants were grown on *Rosa multiflora* understock. Color references are made using The Royal Hortifultural Society (London, England) Colour Chart, 1995, except where common terms of color are used.

For a comparison, several physical characteristics of the rose variety 'Pouljill', U.S. Plant Pat. No. 12,522 are compared to 'Poulcs012' in Chart 1.

CHART 1

| | 'Poulcs012' | 'Pouljill' |
|---|---|---|
| Petalage | 30 to 35 petals | 35 to 40 petals |
| Plant height at full maturity. | 60 cm | 100 cm |
| Upon opening: flower petals inner surface of inner petals. | Yellow Group 4C. | Yellow Group 13B with marginal zone Yellow Group 11D. |

FLOWER AND FLOWER BUD

Blooming habit: Continuous.

Flower bud:

*Size.*—Upon opening, 18 mm in length from base of receptacle to end of bud. Diameter is 15 mm.

*Bud form.*—Broadly ovate to spherical.

*Bud color.*—As sepals unfold, petals are Yellow Group 2C with intonations of Red Group 47A. At ¼ opening Petals are Yellow Group 4D.

*Sepals.*—Upper Surface: Color: Yellow-Green Group 143C with anthocyanic pigments of Greyed-Red Group 181B. Surface: Moderately pubescent, in comparison to the species. Lower Surface: Color: Yellow-Green Group 143C with anthocyanic pigments of Greyed-Purple Group 184C. Texture: Smooth with abundant and very fragrant stipitate glands. Sepal Shape: Sepal apex is cirrhose. Base is flat at union with receptacle. Sepal Margin: Margins have strong foliaceous appendages on three of the five sepals. Size: 18 mm (l)×8 mm (w).

*Receptacle.*—Surface Texture: Smooth and glabrous. Shape: Funnel shaped. Size: 4 mm (h)×6 mm (w). Color: Yellow-Green Group 144A. Anthocyanic pigments the color of Greyed-Orange Group 167A observed.

*Pedicel.*—Surface: Heavy stipitate glands and fragrant. Length: 20 to 25 mm average length. Diameter: 3 mm on average. Color: Yellow-Green Group 144B. Weak anthocyanic pigments the color of Greyed-Red Group 180B observed. Strength: Strong.

*Borne.*—In clusters of 21 flowers, 7 buds per individual flowering stem.

*Peduncle.*—Length: 60 to 100 mm. Diameter: Normally 4 mm. Color: Yellow-Green Group 144B. Texture: Smooth.

Flower bloom:

*Fragrance.*—Moderate wild rose scent.

*Duration.*—The blooms have a duration on the plant of approximately 10 to 14 days. After flowers completely mature, petals fall cleanly away from plant.

*Size.*—Flower diameter is 53 mm when open. Flower depth is 27 mm on average.

*Form.*—Calathiform. Shape of flower when viewed from the side: Upon opening, upper part: Flat. Upon opening, lower part: Flat. Open flower, upper part: Flat. Open flower, lower part: Concave.

Petalage: Average range is 30 to 35 petals under normal conditions with 10 petaloids.

Color:

Upon opening, petals:

*Outermost petals.*—Outer side: Yellow Group 4D. Innder Side: Yellow Group 4C.

*Innermost petals.*—Outer side: Yellow Group 4D. Inner Side: Yellow Group 4C.

After opening, petals:

*Outermost petals.*—Outer side: Yellow Group 4D. Inner Side: Yellow Group 4C.

*Innermost petals.*—Outer side: Yellow Group 4D. Inner Side: Yellow Group 4C.

General tonality: On open flower Yellow Group 4D. No change in the general tonality at the end of the tenth day.

Petals:

*Petal reflex.*—Somewhat reflexed.

*Margin.*—Entire and uniform. Weak to medium undulations of margin observed.

*Shape.*—Apex: Round. Base: Acute. Petals are generally broadly elliptic.

*Size.*—35 mm (l)×32 mm (w).

*Texture.*—Smooth.

*Thickness.*—Average.

*Arrangement.*—Not formal.

Petaloids:

*Quantity.*—8 to 12.

*Color.*—Upper Surface: Yellow Group 4C. Lower Surface: Yellow Group 4D.

*Size.*—30 mm (l)×28 mm (w).

*Shape.*—Elliptical. Base and apex are acute.

Reproductive organs:

*Pistils.*—Length: 5 mm long. Quantity: 59 (approximately).

*Pollen.*—None observed.

*Anthers.*—Size: 1 to 2 mm in length. Color: Greyed-Orange Group 163B. Quantity: 99 (approximately).

*Filaments.*—Color: Yellow Group 9A. Length: 4 mm.

*Stigmas.*—Superior relative to the length of filaments and to the height of the anthers. Color: Greyed-Yellow Group 162A.

*Styles.*—Color: Yellow-Green Group 150D. Other Intonations: Red-Purple Group 57A.

*Hips.*—None Observed in the field nursery in Jackson County Oreg.

PLANT

Plant growth: Moderate, upright to bushy. When grown as a budded field grown plant on *Rosa multiflora* understock, the average height of the plant is 60 cm and the average width is 60 cm.

Stems:

*Color.*—Young wood: Yellow-Green Group 144B. Older wood: Yellow-Green Group 144B.

*Surface texture.*—Young wood: Smooth. Older wood: Smooth.

Thorns:

*Incidence.*—4 thorns per 10 cm of stem.

*Size.*—9 mm.

*Color.*—Greyed-Orange Group 177B.

*Shape.*—Deeply concave.

Plant foliage: Normal number of leaflets on normal leaves in middle of the stem: 5 leaflets.

*Compound leaf size.*—150 mm in length by 120 mm wide.

*Quantity.*—On average, there are 3 leaves per 10 cm of stem.

*Color.*—Mature Foliage: Upper surface is: Green Group 137A to Yellow-Green Group 144A. Lower surface is: Yellow-Green Group 147C. Juvenile foliage: Upper surface is: Yellow-Green Group 144A. Lower surface is: Yellow-Green Group 144B.

Plant leaves and leaflets:

*Stipules.*—Size: 20 mm in length. Shape: Linear with outward extending apices. The apex is acute. Base is flat at the union with the petiole. Quantity: 2 per compound leaf. Margins: Finely serrated with abundant stipitate glands. Color: Yellow-Green Group 144A.

*Petiole.*—Length: 25 mm. Above: Color: Yellow-Green Group 144B. Underneath: Observations: Thorns observed. Color: Yellow-Green Group 144A.

*Rachis.*—Length: 53 mm. Above: Color: Yellow-Green Group 144B. Underneath: Observations: Thorns observed. Color: Yellow-Green Group 144A.

*Leaflet.*—Edge: Serrated. Size: 45 to 68 mm (l)×25 to 42 mm (w). Shape: Ovate. Apex is cuspidate. Base is round. Texture: Smooth. Thickness: Thick. Arrangement: Odd pinnate. Venation: Reticulate. Glossiness: Glossy.

Disease resistance: Above average resistance to mildew, rust, black spot, and *Botrytis* under normal growing conditions in Jackson County, Oreg.

Cold hardiness: The variety 'Poulcs012' has been found to be cold tolerant to USDA Cold Hardiness Zone 6.

It is claimed:

1. A new and distinct variety of rose plant of the floribunda rose class named 'Poulcs012', substantially as herein illustrated and described as a distinct and novel rose variety due to its abundant light yellow flowers, disease resistance, and extended period of bloom.

* * * * *

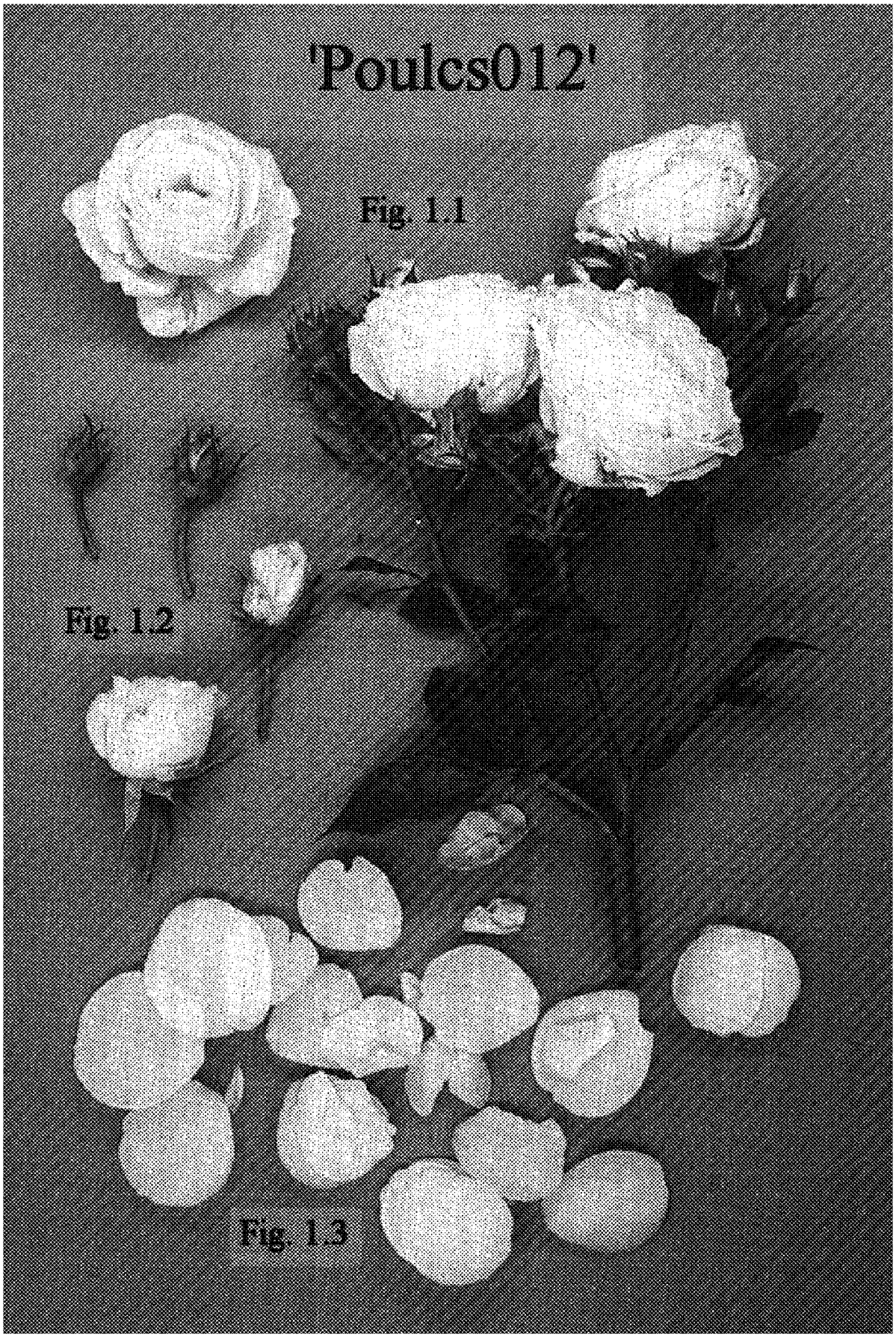
'Poulcs012'
Fig. 1.1
Fig. 1.2
Fig. 1.3

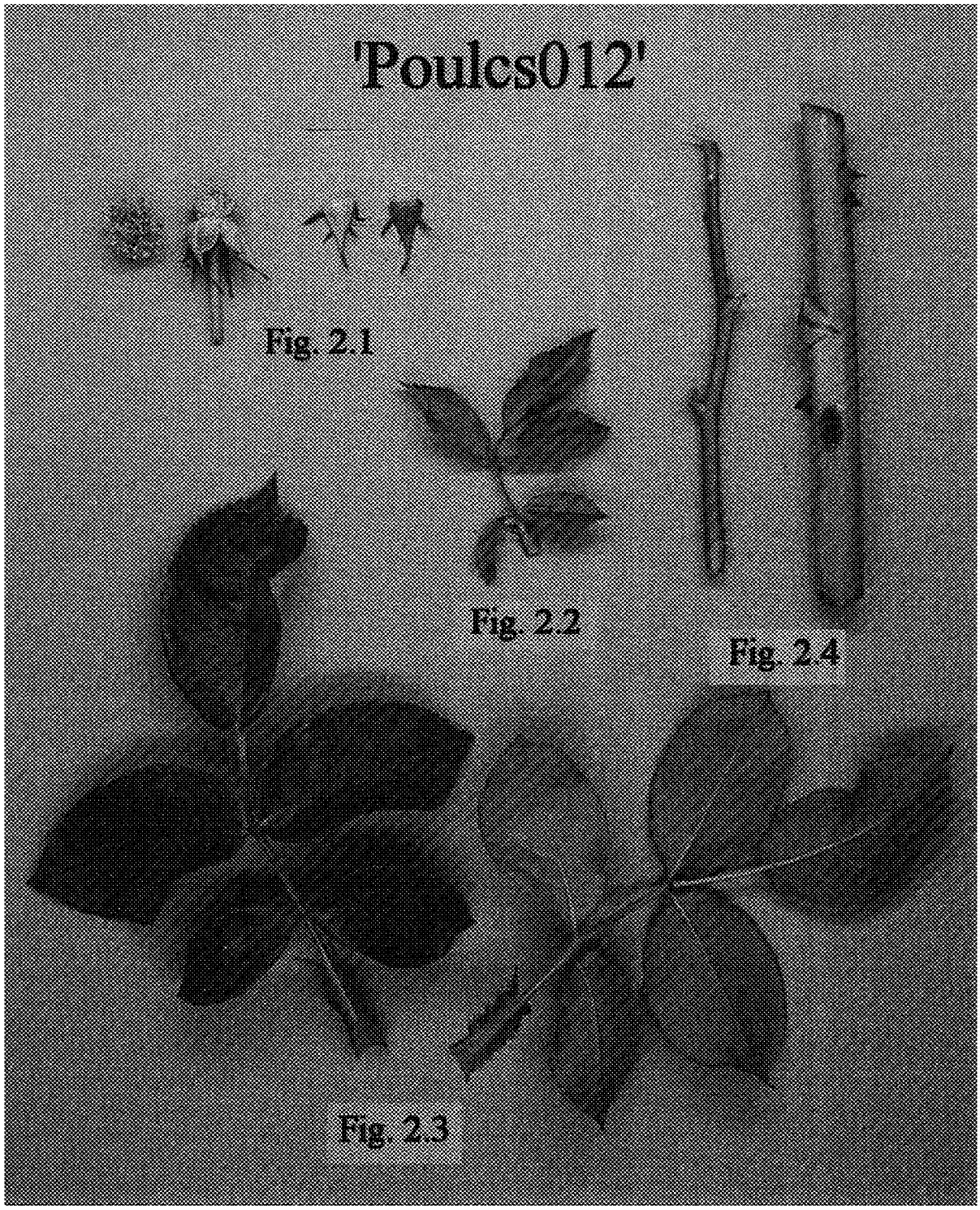
'Poulcs012'
Fig. 2.1
Fig. 2.2
Fig. 2.4
Fig. 2.3